US010354007B2

(12) United States Patent
Sharma et al.

(10) Patent No.: US 10,354,007 B2
(45) Date of Patent: Jul. 16, 2019

(54) SYSTEM AND METHOD FOR CONFIGURING CLINICAL WORKFLOWS AND GENERATING USER INTERFACES THEREOF

(71) Applicant: Cognizant Technology Solutions India Pvt. Ltd., Chennai (IN)

(72) Inventors: Sandeep Kumar Sharma, Bangalore (IN); Abhijeet Dutta, Bangalore (IN); Akshay Dosi, Bangalore (IN); Rahul, Bangalore (IN)

(73) Assignee: COGNIZANT TECHNOLOGY SOLUTIONS INDIA PVT. LTD., Chennai (IN)

( * ) Notice: Subject to any disclaimer, the term of this patent is extended or adjusted under 35 U.S.C. 154(b) by 1010 days.

(21) Appl. No.: 14/714,230

(22) Filed: May 15, 2015

(65) Prior Publication Data
US 2015/0332197 A1  Nov. 19, 2015

(30) Foreign Application Priority Data

May 16, 2014 (IN) .......................... 2446/CHE/2014

(51) Int. Cl.
| | | |
|---|---|---|
| *G06Q 10/06* | (2012.01) | |
| *G06F 17/27* | (2006.01) | |
| *G06F 17/28* | (2006.01) | |
| *G06Q 50/22* | (2018.01) | |
| *G16H 40/20* | (2018.01) | |
| *G16H 50/20* | (2018.01) | |

(52) U.S. Cl.
CPC .......... *G06F 17/2765* (2013.01); *G06F 17/28* (2013.01); *G06Q 10/06316* (2013.01); *G06Q 50/22* (2013.01); *G16H 40/20* (2018.01); *G16H 50/20* (2018.01)

(58) Field of Classification Search
None
See application file for complete search history.

(56) References Cited

U.S. PATENT DOCUMENTS

2004/0172294 A1* 9/2004 Dahlin ............... G06Q 10/0633
705/2
2008/0270438 A1* 10/2008 Aronson ................ G16H 10/40
(Continued)

*Primary Examiner* — Michael Tomaszewski
(74) *Attorney, Agent, or Firm* — Cantor Colburn LLP

(57) ABSTRACT

A computer-implemented method, system and computer program product for defining clinical workflows is provided. The computer-implemented comprises receiving, at a server-end, information related to one or more clinical workflows. The computer-implemented method further comprises translating the received information into a machine readable language, wherein the received information is translated by splitting the received information into one or more structural components and translating each of the one or more structural components. Furthermore, the computer-implemented method comprises storing the translated information as metadata. Also, the computer-implemented method comprises synchronizing the stored metadata with one or more client devices to define the one or more clinical workflows in the one or more client devices, wherein the one or more defined clinical workflows are dynamically customized based on one or more patient parameters.

16 Claims, 8 Drawing Sheets

(56) References Cited

U.S. PATENT DOCUMENTS

| | | | | |
|---|---|---|---|---|
| 2009/0182575 A1* | 7/2009 | Warner | ............... | G06Q 10/06 |
| | | | | 705/2 |
| 2013/0041677 A1* | 2/2013 | Nusimow | ............ | G06Q 50/22 |
| | | | | 705/2 |
| 2013/0085771 A1* | 4/2013 | Ghanbari | ............ | G16H 10/60 |
| | | | | 705/2 |

\* cited by examiner

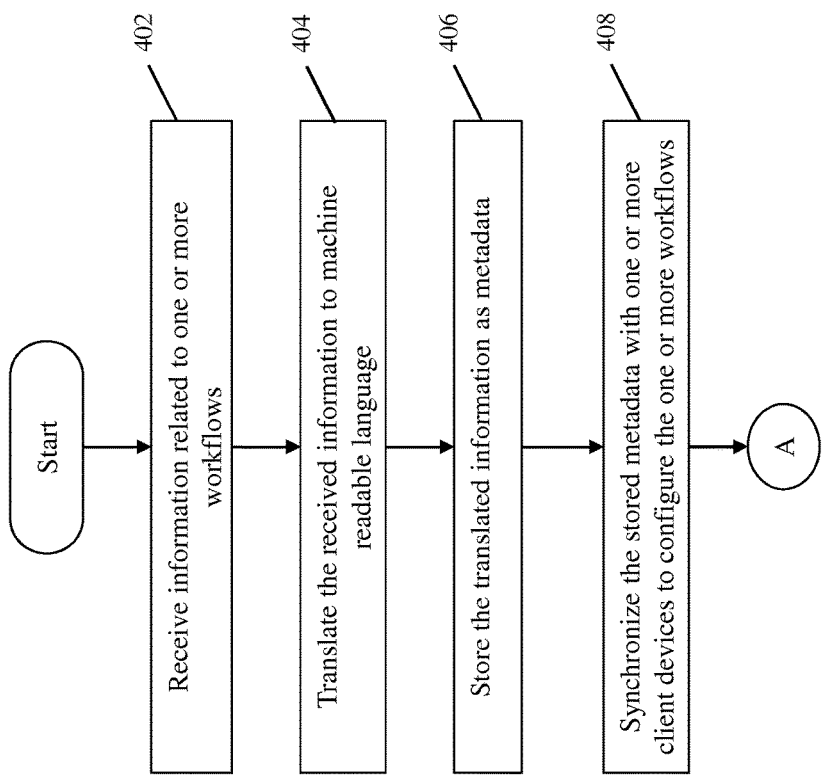

SYSTEM AND METHOD FOR CONFIGURING CLINICAL WORKFLOWS AND GENERATING USER INTERFACES THEREOF

FIELD OF THE INVENTION

The present invention relates generally to defining clinical workflows. More particularly, the present invention provides a system and method for automatically defining clinical workflows and dynamically generating user interfaces related to the defined clinical workflows.

BACKGROUND OF THE INVENTION

In healthcare industry, healthcare personnel follow various clinical workflows for diagnosis and treatment of medical disorders. Typically, a clinical workflow is a series of steps for diagnosing and treating a medical disorder. For example, a doctor attending to a patient suffering from chest pain often first measures blood pressure and pulse and then records Electro Cardio Graph (ECG) followed by a diagnosis and subsequent treatment using the measured parameters. Usually, clinical workflows followed by healthcare personnel depend on various factors such as patient's medical history, habits, age, weight and gender.

Conventionally, various systems and methods exist for providing clinical workflows to healthcare personnel in healthcare facilities. For example, in most healthcare facilities, either the clinical workflows are implemented by each healthcare person based on his knowledge, skill, specialty and expertise or exist in the form of paper manuals and clinical guidelines. However, the abovementioned workflows suffer from various disadvantages. Firstly, since these workflows are not standardized and vary based on hospital's clinical protocols and availability of support equipment, they are implemented in different manner by different healthcare personnel. Secondly, since they may not be available at patient point of care, different healthcare personnel at different locations and different times may apply them in different fashion based on their experience. Thirdly, demographic and patient profiles also play a role in modifying these workflows which is generally not desirable.

To overcome the abovementioned disadvantages, various Information Technology (IT) systems have been designed to bring uniformity to the workflows for healthcare industry. However, these systems also suffer from various disadvantages. Firstly, there is a requirement to define clinical workflows by clinician or care providers and configure these into the IT system prior to deployment. Secondly, it is cumbersome to modify the already deployed workflows and difficult to make even minor customizations. Even if some systems facilitate customizations, the cost of doing so is very high and requires skilled software developers, which is generally an expensive proposition. Therefore, the existing system also fails to deliver efficient and uniform healthcare services at organization as well as patient level.

In light of the above, there is a need for a system and method that facilitates users to define clinical workflows. Further, there is a need for a system and method that facilitates the users to define clinical workflows as per the needs of the healthcare facility after deployment. Furthermore, there is a need for a system and method which is scalable to accommodate additional clinical workflows and does not require redeployment and patches for customization and modifications. In addition, there is a need for a system and method which is rules centric and rules can be provided by the user with minimum efforts. Also, there is a need for a system and method that provides uniform clinical workflows and reduces dependency on presence of doctors, specialist care providers and clinicians. Further, there is a need for a system and method which invokes clinical workflows based on pre-stored information and latest patient parameters and suggests further steps of workflows to diagnose disorder. Moreover, there is a need for a system and method that facilitates creating interactive user interface screens based on the workflows. Further, there is a need for a system and methods that efficiently generates customized user interface screens for existing as well as new healthcare applications. Furthermore, there is a need for a system and method that allows creating, modifying and customizing user interface screens without any need for re-deployment or updates with respect to the healthcare applications. In addition, there is a need for a system and method that reduces development and deployment time of an application having similar user interface screens and facilitates implementing new features without following complete software development lifecycle.

SUMMARY OF THE INVENTION

A computer-implemented method, system and computer program product for defining clinical workflows is provided. The computer-implemented method comprises receiving, at a server-end, information related to one or more clinical workflows, via program instructions stored in a memory and executed by a processor. The computer-implemented method further comprises translating the received information into a machine readable language, wherein the received information is translated by splitting the received information into one or more structural components and translating each of the one or more structural components. In addition, the computer-implemented method comprises storing the translated information as metadata, wherein the step of storing the translated information as the metadata comprises storing the translated information for each of the one or more structural components and their association with other structural components as the metadata. Also, the computer-implemented method comprises synchronizing the stored metadata with one or more client devices to define the one or more clinical workflows in the one or more client devices, wherein the one or more defined clinical workflows are dynamically customized based on one or more patient parameters.

In an embodiment of the present invention, the computer-implemented method further comprises receiving, at the one or more client devices, values of the one or more patient parameters from at least one of: one or more healthcare providers and one or more medical devices. Furthermore, the computer-implemented method comprises matching each of the received values of the one or more patient parameters with pre-stored reference values for triggering the one or more defined workflows, wherein the synchronized metadata comprises the pre-stored reference values for triggering. In addition, the computer-implemented method comprises triggering a defined workflow associated with the pre-stored reference value that matches at least one of the received value of the at least one parameter. The computer-implemented method also comprises rendering one or more steps of the triggered workflow using at least one of: the synchronized metadata corresponding to the triggered workflow and additional information received from at least one of: the one or more healthcare providers and the one or more medical devices.

In an embodiment of the present invention, the step of rendering the one or more steps of the triggered workflow comprises modifying a standard User Interface (UI) template dynamically based on the synchronized metadata to generate one or more UI screens of the triggered workflow, wherein the standard UI template is modified by applying one or more pre-stored UI generation rules and one or more pre-stored rules related to user interaction elements. The step of rendering the one or more steps of the triggered workflow further comprises rendering the generated one or more UI screens on the one or more client devices.

In an embodiment of the present invention, the received information related to the one or more clinical workflows comprise at least one of: one or more trigger conditions, one or more reference values for triggering, one or more pathways, one or more clinical rules, one or more business rules, one or more exit conditions and information related to one or more User Interface (UI) screens associated with each of the one or more clinical workflows.

In an embodiment of the present invention, the one or more patient parameters comprise: body temperature, blood pressure, heart rate, blood glucose level, and blood oxygen level. In an embodiment of the present invention, the one or more healthcare providers comprise doctors, specialists, nurses and clinicians. In an embodiment of the present invention, the one or more medical devices comprise thermometer, blood pressure measuring device, electrocardiography device, glucometer, pulse oximeter and arterial blood gas measurement device.

The system for defining clinical workflows comprises a user interface, at a server-end, configured to receive information related to one or more clinical workflows. The system further comprises an interpreter configured to translate the received information into a machine readable language, wherein the received information is translated by splitting the received information into one or more structural components and translating each of the one or more structural components. Furthermore, the system comprises a metadata convertor configured to store the translated information as metadata in a server metadata repository, wherein storing the translated information comprises storing the translated information for each of the one or more structural components and their association with other structural components as metadata. Also, the system comprises a workflow configuration engine configured to synchronize the stored metadata with one or more client devices to define one or more clinical workflows in the one or more client devices, wherein the synchronization is facilitated at the one or more client devices by a Software Development Kit (SDK) and further wherein the one or more defined workflows are dynamically customized based on one or more patient parameters.

In an embodiment of the present invention, the SDK comprises a client user interface configured to receive values of the one or more patient parameters from at least one of: one or more healthcare providers and one or more medical devices. The SDK further comprises a workflow processing engine configured to match each of the received values of the one or more patient parameters with pre-stored reference values for triggering the one or more defined workflows, wherein the synchronized metadata comprises the pre-stored reference values for triggering. The workflow processing engine is further configured to trigger a defined workflow associated with the pre-stored reference value that matches at least one of the received value of the at least one parameter. Furthermore, the workflow processing is configured to render one or more steps of the triggered workflow using at least one of: the synchronized metadata associated with the triggered workflow and additional information received from at least one of: the one or more healthcare providers and the one or more medical devices.

In an embodiment of the present invention, rendering the one or more steps of the triggered workflow comprises modifying a standard User Interface (UI) template dynamically based on the synchronized metadata to generate one or more UI screens of the triggered workflow, wherein the standard UI template is modified by applying one or more pre-stored UI generation rules and one or more pre-stored rules related to user interaction elements. Further, rendering the one or more steps of the triggered workflow comprises rendering the generated one or more UI screens on the one or more client devices.

The computer program product for defining clinical workflows comprises a non-transitory computer-readable medium having computer-readable program code stored thereon, the computer-readable program code comprising instructions that when executed by a processor, cause the processor to receive, at a server-end, information related to one or more clinical workflows. The processor further translates the received information into a machine readable language, wherein the received information is translated by splitting the received information into one or more structural components and translating each of the one or more structural components. Furthermore, the processor stores the translated information as metadata, wherein the step of storing the translated information as the metadata comprises storing the translated information for each of the one or more structural components and their association with other structural components as the metadata. The processor also synchronizes the stored metadata with one or more client devices to define the one or more clinical workflows in the one or more client devices, wherein the one or more defined clinical workflows are dynamically customized based on one or more patient parameters.

A computer-implemented method, system and computer program product for generating one or more User Interface (UI) screens is provided. The computer-implemented method comprises receiving information related to UI screens, via program instructions stored in a memory and executed by a processor. Furthermore, the computer-implemented method comprises modifying a standard UI template dynamically based on the received information to generate one or more UI screens, wherein the standard UI template is modified by applying one or more pre-stored UI generation rules and one or more pre-stored rules related to user interaction elements. The computer-implemented method also comprises rendering the one or more generated UI screens on one or more client devices.

In an embodiment of the present invention, the received information related to UI screens comprises at least: number of the user interaction elements, type of the user interaction elements and placement of the user interaction elements on a UI screen. In an embodiment of the present invention, the user interaction elements comprise at least one of: a radio button, a banner, a text box, a list box, a check box, a drop-down list, a window, a datagrid, a slider, an icon and a menu bar.

In an embodiment of the present invention, the step of modifying the standard UI template comprises placing one or more user interaction elements on the standard UI template based on the received information and modifying the configuration and attribute details of the standard UI template based on the modifications to the standard UI template.

The system for generating one or more UI screens comprises an input module configured to receive information related to UI screens. Further, the system comprises a UI metadata repository configured to store at least: one or more pre-stored UI generation rules, one or more pre-stored rules related to the user interaction elements and the received information. Furthermore, the system comprises a UI processing engine configured to modify a standard UI template dynamically based on the received information to generate one or more UI screens, wherein the standard UI template is modified by applying the one or more pre-stored UI generation rules and the one or more pre-stored rules related to the user interaction elements. The UI processing engine is further configured to render the one or more generated UI screens on one or more client devices.

In an embodiment of the present invention, modifying the standard UI template, by the UI processing engine, comprises placing one or more user interaction elements on the standard UI template based on the received information and modifying the configuration and attribute details of the standard UI template based on the modifications to the standard UI template.

The computer program product for generating one or more User Interface (UI) screens comprises a non-transitory computer-readable medium having computer-readable program code stored thereon, the computer-readable program code comprising instructions that when executed by a processor, cause the processor to receive information related to UI screens. The processor further modifies a standard UI template dynamically based on the received information to generate one or more UI screens, wherein the standard UI template is modified by applying one or more pre-stored UI generation rules and one or more pre-stored rules related to user interaction elements. Furthermore, the processor renders the one or more generated UI screens on one or more client devices.

BRIEF DESCRIPTION OF THE ACCOMPANYING DRAWINGS

The present invention is described by way of embodiments illustrated in the accompanying drawings wherein:

FIGS. 4A and 4B represent a flowchart of a method for defining clinical workflows, in accordance with an embodiment of the present invention;

DETAILED DESCRIPTION OF THE INVENTION

A system and method for defining clinical workflows is described herein. The invention provides for a system and method that facilitates users to define clinical workflows as per the needs of a healthcare facility. Further, the invention provides for a system and method which is scalable to accommodate additional clinical workflows and does not require redeployment and patches for customization and modifications. Furthermore, the invention provides for a system and method which is rules centric and rules can be provided by the user with minimum efforts. In addition, the invention provides for a system and method that provides uniform clinical workflows and reduces dependency on presence of doctors, specialist care providers and clinicians. Also, the invention provides for a system and method which invokes clinical workflows based on pre-stored information and latest patient parameters and dynamically suggests further steps of workflows to diagnose disorder. The invention further provides for a system and method that is capable of altering subsequent steps of the clinical workflows based on patient information and user inputs provided in previous steps of the clinical workflows. Furthermore, the invention provides for a system and method that facilitates creating interactive user interface screens based on the workflows. In addition, the invention provides for a system and method that allows creating, modifying and customizing user interface screens without any need for re-deployment or new releases of the healthcare applications. In addition, there is a need for a system and method that reduces development time of an application having similar user interface screens and facilitates implementing new features without following complete software development lifecycle.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention would now be discussed in context of embodiments as illustrated in the accompanying drawings.

Figure 1:
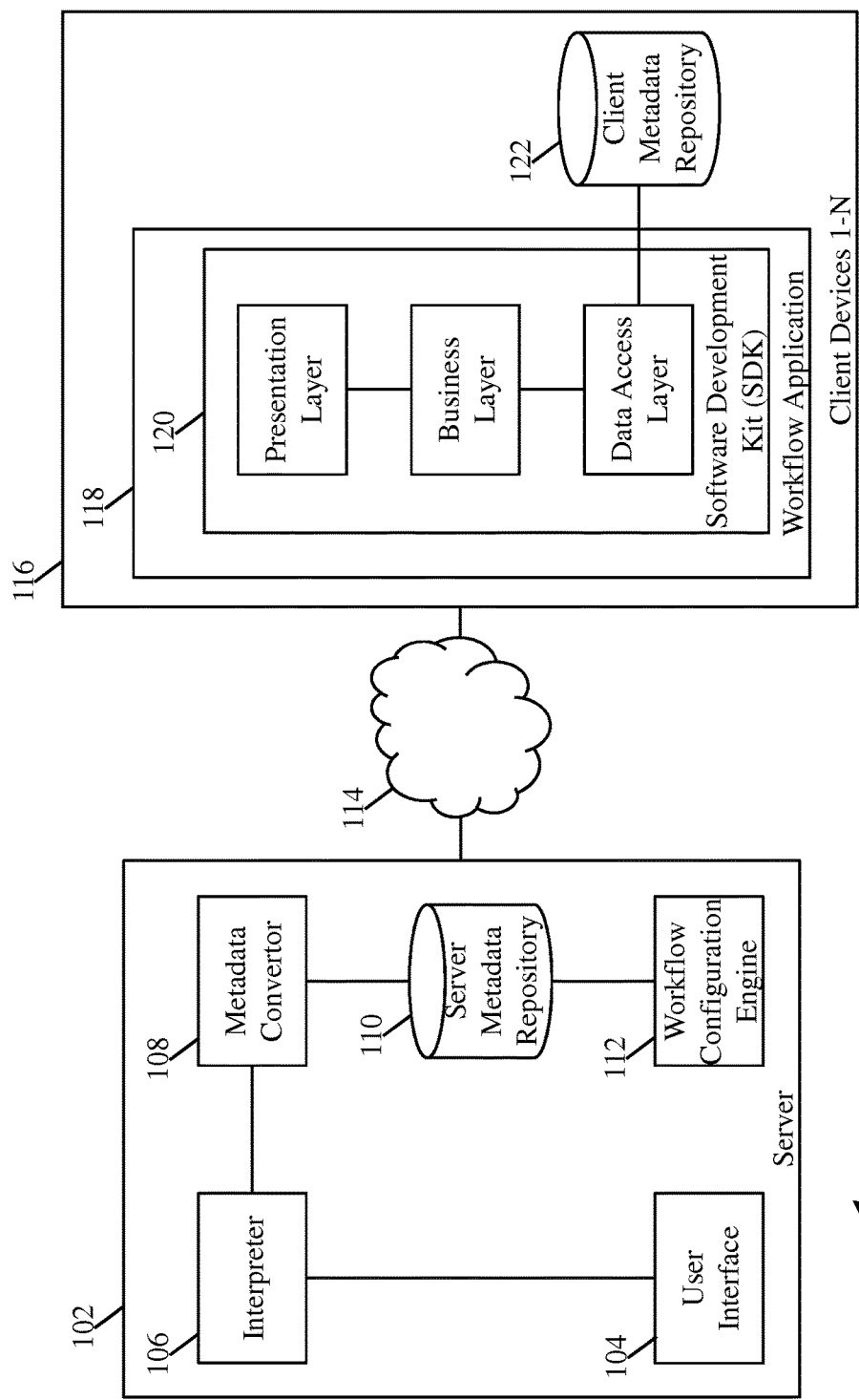
FIG. 1 is a block diagram illustrating a system for defining one or more clinical workflows, in accordance with an embodiment of the present invention.

FIG. 1 is a block diagram illustrating a system for defining one or more clinical workflows, in accordance with an embodiment of the present invention. The system 100 comprises a server 102 in communication with one or more client devices 116. The server 102 comprises a user interface 104, an interpreter 106, a metadata convertor 108, a server metadata repository 110 and a workflow configuration engine 112.

The user interface 104 is a front end interface configured to receive information related to one or more clinical workflows. The one or more clinical workflows (hereinafter also referred to as workflows) are a series of steps that are implemented for diagnosis of health condition and treatment of one or more patients by one or more healthcare providers. The one or more workflows implemented by the one or more healthcare providers depend on various factors such as, but not limited to, condition of the patient, medical history, age, weight and gender.

In an embodiment of the present invention, the one or more healthcare providers include, but are not limited to, doctors, specialists, nurses and clinicians. In an embodiment of the present invention, the received information related to the one or more workflows includes at least one of: one or more trigger conditions, one or more reference values for triggering, one or more pathways, one or more clinical rules, one or more business rules, one or more exit conditions and information related to one or more user interface screens associated with each of the one or more workflows. In an exemplary embodiment of the present invention, the information related to the one or more workflows is received in English language and semantically equivalent phrases such as, but not limited to, greater than, less than, equal to, start and stop.

Figure 1A:
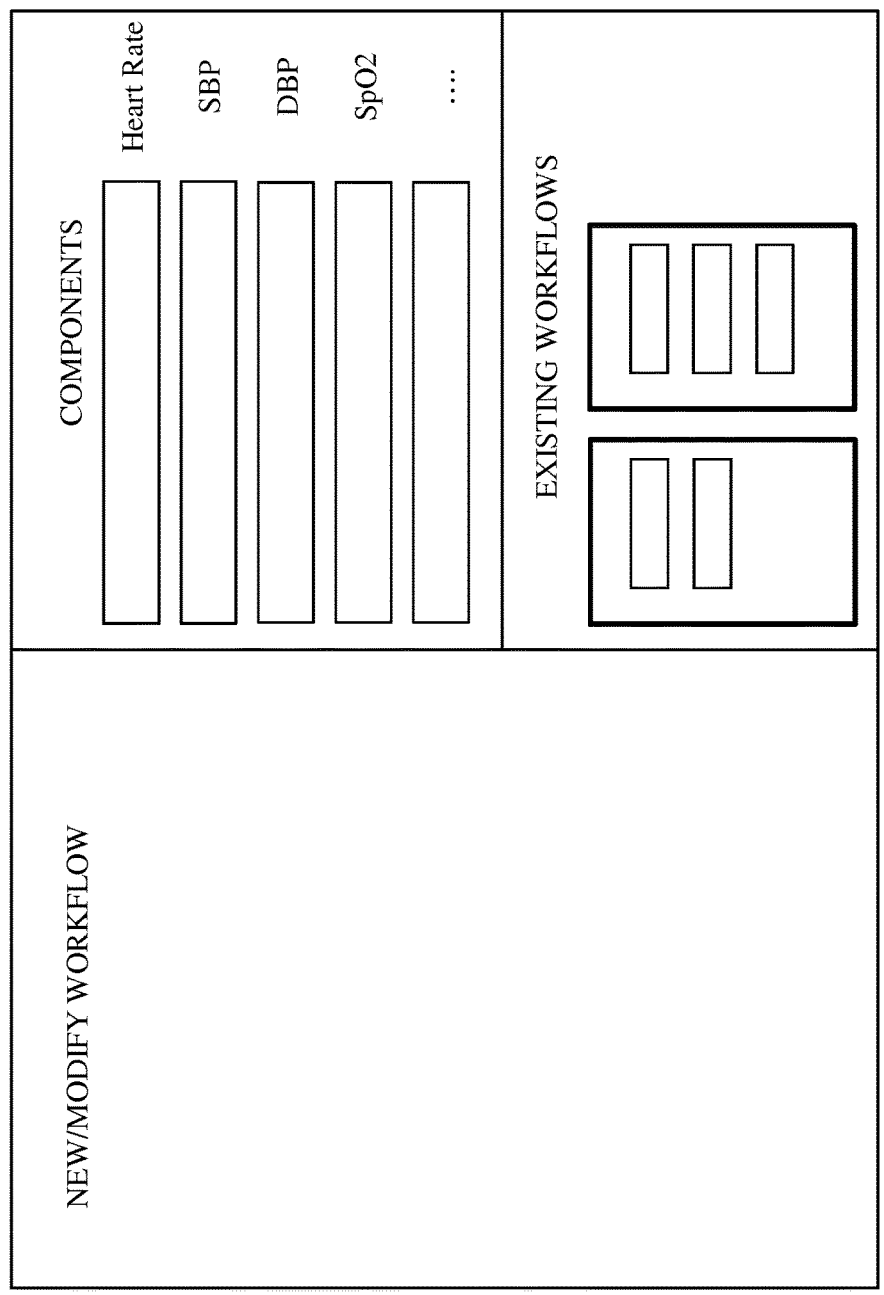
FIG. 1A is a graphical user interface for creating new workflows and modifying and deleting existing workflows, in accordance with an exemplary embodiment of the present invention.

In an embodiment of the present invention, the user interface 104 provides a graphical user interface having drag and drop tools for creating, modifying and deleting the one or more workflows. FIG. 1A is a graphical user interface for creating new workflows and modifying and deleting existing workflows, in accordance with an exemplary embodiment of the present invention. In an exemplary embodiment of the present invention, the user interface 104 provides options to the one or more healthcare providers to create the one or more workflows using spreadsheets. In an embodiment of the present invention, a healthcare provider authorized to create new workflows logs in to the server 102 via the user interface 104 by providing authentication details. The healthcare provider then creates a new workflow by entering a name and description of the new workflow to be created. The healthcare provider then provides input and output parameters and defines one or more steps of the new workflow. In another embodiment of the present invention, the healthcare provider may modify an exiting workflow by selecting the existing workflow from a list of all existing workflows rendered on the user interface 104.

The interpreter 106 is configured to translate the received information related to the one or more workflows into a machine readable language. In an embodiment of the present invention, the interpreter 106 identifies one or more structural components of the received information by splitting the received information. The interpreter 106 then translates each of the one or more identified structural components to a set of machine understandable entities using Data Descriptive Language (DDL) based on pre-defined parsing rules stored in the interpreter 106. In an embodiment of the present invention, the received information is translated to Extensible Markup Language (XML) by the interpreter 106 using pre-stored XML configurations. The pre-stored XML configurations are defined and stored for each of the one or more structural components at the time of designing the system 100. Further, the pre-stored XML configurations can be modified and new configurations can be added via the user interface 104. The interpreter 106 also facilitates storing the received information and the translated information in the server 102.

In an exemplary embodiment of the present invention, a clinical rule comprising a reference value such as: "If Systolic Blood Pressure<90, Call for Urgent Backup" is split into its structural components and expressed in machine understandable language as:

Input ID: 1
Input Parameter: Systolic Blood Pressure
Action: Less Than <
Reference: 90
Output: Call for Urgent Backup In an exemplary embodiment of the present invention, part of a clinical rule such as: "mental status of a patient=normal or altered" is translated as:
Input ID: 2
Input Value: Mental Status
Input Type: Choice
Input Options: Normal, Altered The metadata convertor 108 stores the translated information in the form of machine readable language as metadata. The metadata convertor 108 comprises logic and code to store the translated information corresponding to each structural component along with its association with other structural components as metadata in the server metadata repository 110. The stored metadata defines relationships between various data sets, data values and data sources of the server metadata repository 110. The metadata convertor 108 also associates each structural component to a corresponding User Interface (UI) component and stores the associated data as UI metadata. In an embodiment of the present invention, the metadata is stored in the form of, but not limited to, one or more master tables, flat files and Extensible Markup Language (XML) files.

In an embodiment of the present invention, the metadata stored in different tables serves different purposes. In an embodiment of the present invention, the metadata stored in the one or more master tables is used for providing source location for capturing additional data. The metadata also comprises unique identifiers for patient parameters. The metadata defines which patient parameter refers to which value. The metadata further provides details of the table from where the referred value is to be obtained and conditions based on which the referred value is to be obtained. Furthermore, the values of the patient parameters are controlled by flags. The flags associated with a specific patient parameter are used to control updating and purging intervals of the values associated with that patient parameter. In addition, flags are also used to handle movement to next conditions, jump to specific condition and exit points when a workflow is active. The server metadata repository 110 also comprises one or more pre-stored rules, software logic and codes that facilitate storing the metadata for further use and dynamically generating steps of the one or more workflows on the one or more client devices 116. In an embodiment of the present invention, the one or more pre-stored rules define relationships between various data sets, data values and data sources within the server metadata repository 110.

In an embodiment of the present invention, using the metadata for defining the one or more workflows facilitates in modifying the one or more workflows without changing the underlying code. Further, adding and modifying metadata facilitates defining additional workflows and modifying existing workflows.

The workflow configuration engine 112 synchronizes the metadata stored in the server metadata repository 110 with the one or more client devices 116. In an embodiment of the present invention, the server 102 and the one or more client devices 116 communicate via a cloud computing infrastructure 114. In another embodiment of the present invention, the server 102 and the one or more client devices 116 communicate via web service.

The one or more client devices 116 are electronic communication devices that facilitate the one or more healthcare providers attending to the one or more patients to access the one or more workflows. In an embodiment of the present invention, the one or more client devices include, but not limited to, smartphones, tablets, smart watches, wearable computing devices, laptops, desktops and personal digital assistants (PDAs). In another embodiment of the present invention, the one or more client devices 116 are specially manufactured to facilitate the one or more healthcare providers to implement workflows. In an exemplary embodiment of the present invention, the one or more client devices 116 have Android operating system. In another exemplary embodiment of the present invention, the one or more client devices 116 have iOS operating system. In various embodiments of the present invention, the one or more client devices may have any operating system including, but not limited to, iOS, Android, Windows, Ubuntu and Firefox.

In an embodiment of the present invention, the one or more client devices 116 comprise a workflow application 118 and a client metadata repository 122. The one or more client devices 116 also comprise native applications that provide access to device features such as, but not limited to, display screen, camera, microphone, speaker, Bluetooth, database, accelerometer and compass.

The workflow application 118 comprises a Software Development Kit (SDK) 120. The SDK 120 is designed specifically for the operating system of the one or more client devices 116. The SDK 120 facilitates the workflow configuration engine 112 to synchronize the metadata in the server metadata repository 110 with the client metadata repository 122 during workflow application set-up phase. In an embodiment of the present invention, the SDK 120 facilitates in designing the client metadata repository 122 similar to the server metadata repository 110 so that the metadata, one or more pre-stored rules, software logic and codes are synchronized on the one or more client devices 116. In another embodiment of the present invention, the SDK 120 facilitates in synchronizing the metadata in the server metadata repository 110 with the one or more client devices 116 by replicating the server metadata repository 110 in the one or more client devices 116.

In an embodiment of the present invention, during the workflow application set-up phase, the workflow configuration engine 112 communicates with the SDK 120 to configure the one or more master tables in the client metadata repository 122. The one or more master tables configured in the client metadata repository 122 are designed similar to the one or more master tables of the server metadata repository 110. The metadata stored in the one or more master tables at the server 102 is synchronized with the one or more newly configured master tables at the client device 116. In an embodiment of the present invention, the metadata in the one or more master tables of the server 102 is synchronized with the master tables of the client metadata repository 122 at pre-set intervals so that any changes to the metadata in the server 102 are automatically updated on the one or more client devices 116. Further, synchronizing the metadata in the server 102 with the one or more client devices 116 ensures that the workflow application is available even if the one or more client devices 116 are offline and not connected with the server 102. Furthermore, the metadata stored in the client metadata repository 122 is compact and therefore consumes minimal system resources. In an embodiment of the present invention, the client metadata repository 122 is a relational database management system. In an exemplary embodiment of the present invention, the client metadata repository 122 is SQLite.

The SDK 120 also establishes relationships between various tables and facilitates designing and creating one or more transactional tables in the client metadata repository 122. In an embodiment of the present invention, the one or more transactional tables store intermediate information associated with the one or more workflows. The intermediate information associated with the one or more workflows includes, but not limited to, additional information provided by the one or more healthcare providers when the one or more workflows are initiated. The intermediate information also comprises measurements and patient parameters from one or more medical devices and other healthcare enterprise systems such as, but not limited to, laboratory information system and imaging systems. In an embodiment of the present invention, the one or more medical devices include, but are not limited to, thermometer, blood pressure measuring device, electrocardiography device, pulse oximeter and arterial blood gas measurement device. The one or more transactional tables also store information related to functioning of a specific workflow. In an embodiment of the present invention, the one or more transactional tables are periodically synchronized with the server 102 for storage and retrieval of the information via a push mechanism.

Once the metadata is synchronized with the client metadata repository 122, the one or more workflows are defined on the one or more client devices 116 and the workflow application set-up is complete.

The SDK 120 facilitates triggering and customizing the one or more defined workflows based on one or more patient parameters when the one or more healthcare providers access the workflow application 118. The SDK 120 is explained in detail in conjunction with FIG. 2.

Figure 2:
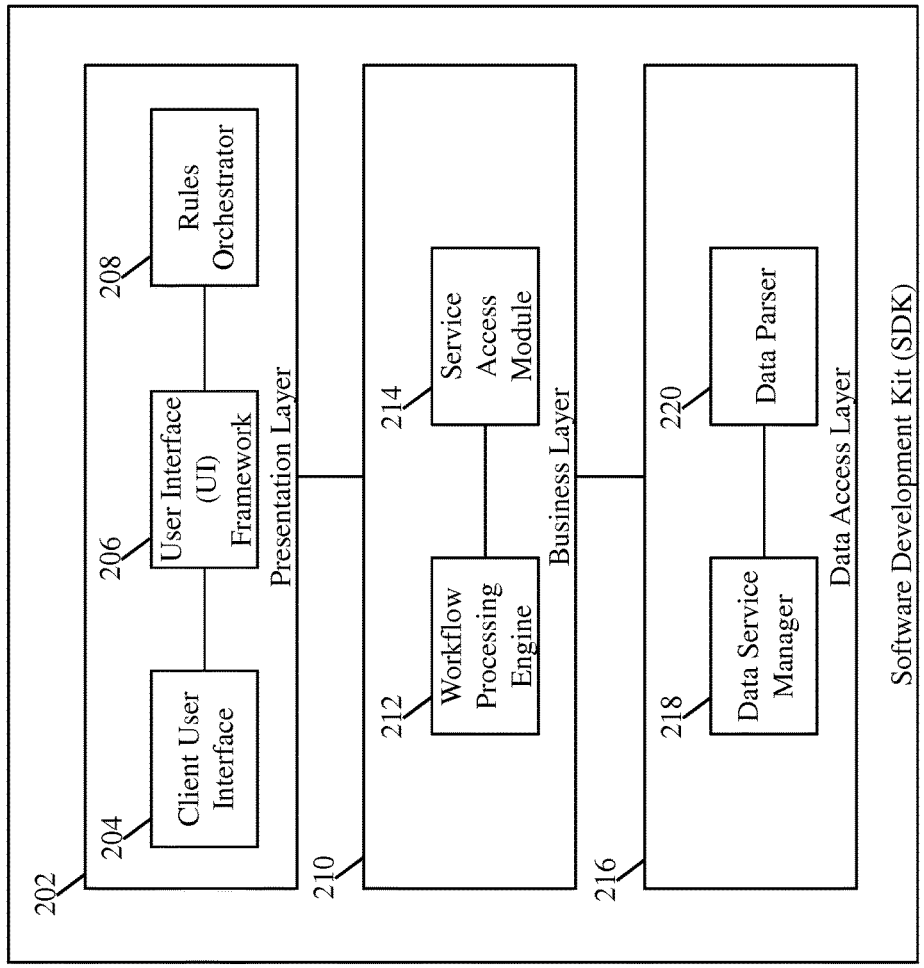
FIG. 2 is a detailed block diagram of a Software Development Kit (SDK), in accordance with an embodiment of the present invention.

FIG. 2 is a detailed block diagram of the SDK, in accordance with an embodiment of the present invention. The SDK 200 comprises a presentation layer 202, a business layer 210 and a data access layer 216.

The presentation layer 202 comprises a client user interface 204, a User Interface (UI) framework 206 and a rules orchestrator 208.

The client user interface 204 is configured to provide options to the one or more healthcare providers to access the workflow application 118 (FIG. 1) while attending to the one or more patients. In an embodiment of the present invention, the one or more healthcare providers provide authentication details to access the workflow application 118 (FIG. 1). In an embodiment of the present invention, the client user interface 204 prompts the one or more healthcare providers to provide patient information such as, but not limited to, patient details and values of the one or more patient parameters and vitals via the client user interface 204. In an embodiment of the present invention, the one or more patient parameters include, but not limited to, body temperature, blood pressure, heart rate, blood glucose level, and blood oxygen level. Once the patient information is provided, the one or more healthcare providers may select one or more defined workflows from a list of defined workflows rendered on the client user interface 204 based on a clinical event or patient factors such as, but not limited to, age, weight, gender, condition of the patient and medical history. The clinical event includes, but not limited to, altered patient parameters. In an embodiment of the present invention, the client user interface 204 communicates with the one or more medical devices and automatically receives values of the one or more patient parameters from the one or more medical devices. The values of the one or more patient parameters received from the one or more healthcare providers or from the one or more medical devices are forwarded to the business layer 210.

The UI framework 206 is configured to facilitate generating the one or more UI screens for the workflow application 118 (FIG. 1). In an embodiment of the present invention, the UI framework 206 communicates with a UI SDK for generating the one or more UI screens. The UI SDK is explained in detail in conjunction with FIG. 3.

The rules orchestrator 208 is configured to receive the synchronized UI metadata associated with the one or more defined workflows from the business layer 210 for generating the one or more UI screens when a defined workflow is triggered. Based on the received metadata, the rules orchestrator 208 communicates with the UI framework 206 to render appropriate user interaction elements on the generated UI screens. The one or more UI screens are generated based on the operating system of the one or more client devices 116.

The business layer 210 is configured to facilitate communication between the presentation layer 202 and the data access layer 216. The business layer 210 comprises a workflow processing engine 212 and a service access module 214.

The workflow processing engine 212 consists of pre-built software logic, business entity definitions and model objects to perform processing using the synchronized metadata stored in the client metadata repository 122 (FIG. 1). The workflow processing engine 212 receives the values of the one or more patient parameters from the one or more healthcare providers or from the one or more medical devices via the presentation layer 202. The workflow processing engine 212 further matches the received values of the one or more patient parameters with pre-stored reference values for triggering the one or more workflows. The workflow processing engine 212 also interprets the metadata and the one or more clinical rules stored in the client metadata repository 122 (FIG. 1) to render steps of the one or more triggered workflows and render appropriate user interface screens comprising one or more steps of the triggered workflow on the client user interface 204.

In an embodiment of the present invention, the workflow processing engine 212 is divided into different sections that handle different conditions. Further, based on the received patient parameters, the workflow processing engine 212 routes the received patient parameters to the specific section containing the logic for processing the values of the received patient parameters using the one or more pre-stored rules. The workflow processing engine 212 continuously monitors the received patient parameters to detect when a triggering condition is met for initiating a defined workflow.

The service access module 214 is configured to communicate with the data access layer 216 for fetching data from the client metadata repository 122 (FIG. 1). The fetched data is used by the workflow processing engine 212 to trigger the one or more defined workflows. In an embodiment of the present invention, the service access module 214 fetches pre-stored reference values for triggering the one or more defined workflows for comparison by the workflow processing engine 212. In another embodiment of the present invention, the service access module 214 fetches data required for rendering one or more steps of a triggered workflow. In an embodiment of the present invention, the service access module 214 comprises code for web services such as, but not limited to, Representational State Transfer (REST), JavaScript Object Notation (JSON), Windows Communication Foundation (WCF) that fetch data from the client metadata repository 122 (FIG. 1).

The data access layer 216 comprises a data service manager 218 and a data parser 220.

The data service manager 218 is configured to handle requests for fetching data received from the service access module 214. The data service manager 218 facilitates access to the client metadata repository 122 (FIG. 1) by handling and forwarding all requests for accessing the client metadata repository 122 (FIG. 1) to the data parser 220.

The data parser 220 is configured to process and parse the received requests for fetching the data from the client metadata repository 122 (FIG. 1). The fetched data is then forwarded to the workflow processing engine 212.

During operation, the three layers within the SDK 200 work in unison. On receiving the values of the one or more patient parameters from the one or more healthcare providers or from the one or more medical devices, the workflow processing engine 212 matches each of the received values of the one or more parameters with the one or more pre-stored reference values for triggering the one or more defined workflows. The one or more pre-stored reference values for triggering the one or more defined workflows and corresponding pre-stored rules are fetched from the client metadata repository 122 (FIG. 1) by the service access module 214 and the data service manager 218. In an embodiment of the present invention, the comparison is performed at pre-determined intervals. In another embodiment of the present invention, the workflow processing engine 212 compares the received value of the parameter with each of the fetched pre-stored reference values whenever a new value of the parameter is received. In an embodiment of the present invention, a pre-stored reference value may be a single value or a range of values that may trigger a workflow.

On comparison, if the workflow processing engine 212 determines that the received value of the patient parameter matches the pre-stored reference value for triggering a defined workflow, then the workflow processing engine 212 provides an indication to the one or more healthcare providers that the particular clinical workflow has been triggered. The workflow processing engine 212 facilitates rendering an appropriate user interface screen on the user interface 204 via the UI framework 206. In an embodiment of the present invention the UI framework 206 communicates with the UI SDK for generating the one or more UI screens of the triggered workflow. In an embodiment of the present invention, the UI SDK modifies a standard UI template dynamically based on the synchronized metadata related to the UI screens to generate the one or more UI screens of the triggered workflow. Further, the standard UI template is modified by applying one or more pre-stored UI generation rules and one or more pre-stored rules related to user interaction elements. This is explained in detail in later sections of the specification. The workflow processing engine 212 then applies pre-stored rules and uses the metadata stored corresponding to the triggered clinical workflow to render one or more steps of the triggered workflow on the client user interface 204. In an embodiment of the present invention, the workflow processing engine 212 performs additional tasks such as, but not limited to, verifying additional conditions, prompting the one or more healthcare providers to provide additional information, receiving additional information from the one or more medical devices, rendering subsequent steps by processing the received additional information and providing appropriate pathways. The additional information received by the workflow processing engine 212 is stored in the one or more transactional tables. The workflow processing engine 212 processes the additional information along with the metadata using the one or more pre-stored rules for dynamically generating and rendering the one or more steps of the triggered clinical workflow on the client user interface 204 until an exit condition for the triggered workflow is reached. The workflow processing engine 212 stores the outcome of the entire workflow once the triggered workflow is completed for future use. The workflow processing engine 212 also records time stamp of each step of the triggered workflow.

In an embodiment of the present invention, if the workflow processing engine 212 determines that the received value of the patient parameter does not match the pre-stored reference value for triggering the one or more defined workflows, then the workflow processing engine 212 waits until another value or set of values of the one or more patient parameters are received.

In an embodiment of the present invention, the workflow processing engine 212 ensures that multiple workflows are not triggered for the same value of received patient parameter. In an embodiment of the present invention, the workflow processing engine 212 ensures that latest patient parameter is received for processing by checking the time stamp of the received patient parameter. In an embodiment of the present invention, the workflow processing engine 212 provides options to the one or more healthcare providers attending to a patient to deactivate a set of clinical workflow from the list of defined clinical workflows rendered on the client user interface 204 based on patient factors.

Figure 3:
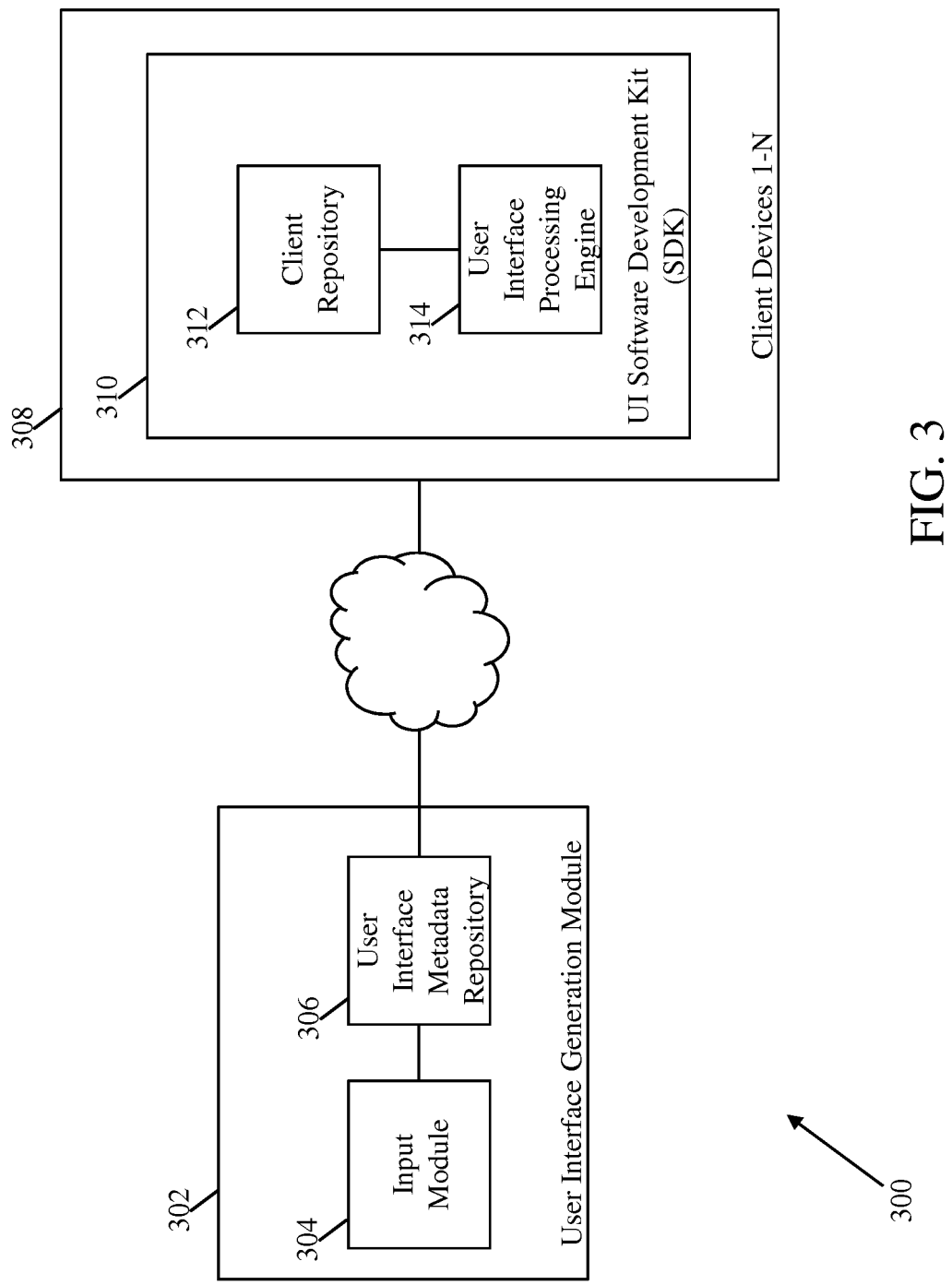
FIG. 3 is a block diagram illustrating a system for generating user interface screens, in accordance with an embodiment of the present invention.

FIG. 3 is a block diagram illustrating a system for generating user interface screens, in accordance with an embodiment of the present invention. The system 300 comprises a User Interface (UI) generation module 302 in communication with the one or more client devices 308. In an embodiment of the present invention, the UI generation module 302 resides in the server 102 (FIG. 1).

The UI generation module 302 comprises an input module 304 and a UI metadata repository 306.

The input module 304 is configured to receive information related to UI screens of one or more applications. In an embodiment of the present invention, the input module 304 facilitates one or more users to provide information related to UI screens of the one or more applications. In another embodiment of the present invention, the workflow processing engine 212 (FIG. 2) provides the synchronized UI metadata related to UI screens via the UI framework 206 (FIG. 2) for generating the one or more UI screens for the clinical workflow application 118 (FIG. 1). In an embodiment of the present invention, the received information related to UI screens include, but is not limited to, components of UI screens, number of user interaction elements, type of user interaction elements, placement of user interaction elements, configuration information for the user interaction elements, order in which the user interaction elements need to be generated and a unique identifier for storing and retrieving the received data related to the UI screens. In an embodiment of the present invention, one or more user interaction elements include, but are not limited to, radio buttons, banners, text boxes, list boxes, check boxes, dropdown lists, windows, datagrids, sliders, icons and menu bars. In an embodiment of the present invention, the input module 304 provides one or more standard UI templates which are filled by the one or more users. The one or more users are then prompted to save the filled template with a unique identification name and description of the UI screen.

The UI metadata repository 306 is configured to store the received information related to the UI screens. The UI metadata repository 306 also comprises metadata required for generating the one or more UI screens based on the stored information related to the UI screens. Further, the UI metadata repository 306 comprises metadata and rules required for synchronizing the metadata and the received information with the one or more client devices 308.

The metadata for generating the one or more UI screens comprise, but not limited to, one or more standard UI templates, identification name and configuration details of various user interaction elements, one or more UI generation rules and one or more rules related to user interaction elements. In an embodiment of the present invention, the one or more standard UI templates are blank UI screens on which various user interaction elements are placed. Further, each of the standard UI templates has its configuration and attribute details stored in the UI metadata repository 306 which is modified for generating the one or more UI screens based on the received information. In an embodiment of the present invention, the one or more UI generation rules comprise, but not limited to, rules for suitably structuring and placing user interaction elements on the UI screens. In an embodiment of the present invention, the one or more rules related to user interaction elements comprise, but not limited to, rules related to placement and configurations of each of the user interaction elements. The one or more user interface generation rules and the one or more rules related to user interaction elements are configurable. In an embodiment of the present invention, these rules are created, modified and deleted via the input module 304 and then stored in the UI metadata repository 306.

In an embodiment of the present invention, the metadata and the received information related to the UI screens are stored in the form of one or more tables. In an exemplary embodiment of the present invention, a UI generation rule related to permissible number of sections in a user interface screen is stored in a particular table. In another exemplary embodiment of the present invention, a table may contain UI generation rule related to permissible number of columns of user interaction elements in each section of the UI screen. In yet another exemplary embodiment of the present invention, the one or more tables comprise information which defines the exact screen location where a user interaction element has to be placed. In yet another exemplary embodiment of the present invention, the one or more tables comprise information related to parameters of each of the one or more user interaction elements. In an exemplary embodiment of the present invention, a parameter related to a text box may permit capturing only date and time in a particular format. The user interaction element placed on the user interface screen will thereby accept only date and time entries. In another exemplary embodiment of the present invention, a parameter related to a text box permits capturing only alphabets. In an exemplary embodiment of the present invention, the user interaction element such as a slider may be configured for inputting a value from a permissible range. In an embodiment of the present invention, the permissible range is received via the input module 304 from the one or more users. In another embodiment of the present invention, the permissible range is received from the workflow processing engine 212 (FIG. 2) via the UI framework 206 (FIG. 2). The one or more rules related to the slider are then applied for placing a slider, on a user interface screen being generated, which will receive input values between the permissible range only.

The UI generation module 302 communicates with a customized UI Software Development Kit (SDK) 310 for generating the one or more UI screens for the one or more client devices 308. The UI SDK 310, within the one or more client devices 308, is operating system specific. The UI SDK 310 comprises a client repository 312 and a UI processing engine 314.

The UI SDK 310 is configured to synchronize the metadata and the received information related to the UI screens stored in the UI metadata repository 306 with the client repository 312. The UI SDK 310 also creates one or more transactional tables in the client repository 312. The one or more transactional tables are configured to store information related to user interaction. In an embodiment of the present invention, the one or more transactional tables also store the unique identification name and description of the UI screens.

Once synchronization of the metadata and the received information with the client repository 312 is complete, the UI SDK 310 facilitates generation of the one or more UI screens of the one or more applications in real-time when the one or more applications are accessed via the one or more client devices 308.

The UI processing engine 314 is configured to modify the one or more pre-stored UI templates based on the received information related to UI screens synchronized with the one or more client devices 308. The UI processing engine 314 modifies the one or more pre-stored UI templates by applying the one or more UI generation rules and the one or more rules related to user interaction elements based on the synchronized information.

In operation, the UI processing engine 314 retrieves a standard UI template and corresponding configuration and attribute details from the client repository 312. The UI processing engine 314 also retrieves the configuration details related to type of the user interaction elements to be placed on the UI screen being generated from the client repository 312. The UI processing engine 314 then retrieves the one or more UI generation rules and the one or more rules related to the user interaction elements to be placed on the UI screen from the client repository 312. Further, the retrieved standard UI template is modified by placing the user interaction elements suitably based on the placement information of the user interaction elements and by applying the retrieved one or more UI generation rules and the one or more rules related to the user interaction elements being placed. The UI processing engine 314 further modifies the retrieved configuration and attribute details of the standard UI template by adding the retrieved configuration details of the user interaction elements being placed on the standard UI template. The UI screen is thereby generated along with its configuration and attribute details.

In an exemplary embodiment of the present invention, the configuration details of the generated UI screens are defined in the client repository 312 using DataBase (DB) driven controls. In another exemplary embodiment of the present invention, the configuration details of the generated UI screens are defined using JavaScript Object Notation (JSON) format. In yet another exemplary embodiment of the present invention, the configuration details of the generated UI screens are defined using XML.

The UI processing engine 314 renders the generated UI screens on the one or more client devices 308. In an embodiment of the present invention, the UI processing engine 314 communicates with the UI framework 206 (FIG. 2) to render the generated UI screens related to the one or more workflows.

Figure 4B:
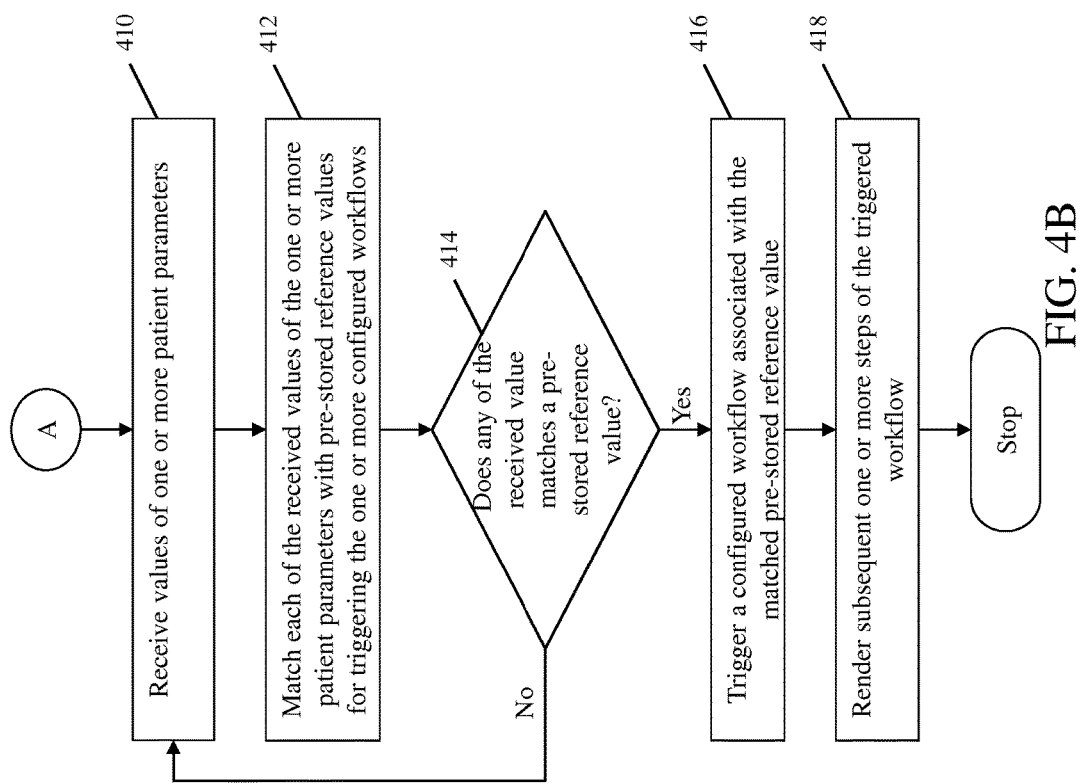

FIGS. 4A and 4B represent a flowchart of a method for defining one or more clinical workflows, in accordance with an embodiment of the present invention.

At step 402, information related to one or more workflows is received at a server-end. The one or more clinical workflows are a series of steps that are to be followed for diagnosis of health condition and treatment of patients by one or more healthcare providers. The one or more healthcare providers include, but are not limited to, doctors, specialists, nurses and clinicians. In an embodiment of the present invention, the received information related to clinical workflows includes, but not limited to, one or more trigger conditions, one or more reference values for triggering, one or more pathways, one or more clinical rules, one or more business rules, one or more exit conditions and information related to one or more user interface screens associated with each of the one or more clinical workflows. In an embodiment of the present invention, the one or more healthcare providers provide information related to the one or more workflows via a user interface at the server-end. In an embodiment of the present invention, a healthcare provider authorized to create new workflows logs in to the server via the user interface by providing authentication details. In an embodiment of the present invention, the user interface at the server-end provides drag and drop tools for creating and modifying the one or more clinical workflows. In another embodiment of the present invention, the user interface at the server-end provides options to the one or more healthcare providers to create and modify the one or more clinical workflows using spreadsheets. The received information is stored in the server.

At step 404, the received information related to the one or more workflows is translated into machine readable language and stored in the server. In an embodiment of the present invention, an interpreter facilitates identifying and splitting the received information into the one or more structural components. The interpreter then translates each of the one or more identified structural components to a set of machine understandable entities using Data Descriptive Language (DDL) based on pre-defined parsing rules. In an embodiment of the present invention, the received information is translated to Extensible Markup Language (XML) using pre-stored XML configurations. The pre-stored XML configurations are defined for each of the one or more structural components. Further, the pre-stored XML configurations can be modified and new configurations can be added via the user interface.

At step 406, the translated information in the form of machine readable language is stored as metadata in a repository. In an embodiment of the present invention, the step of storing the translated information comprises storing the translated information for each of the one or more structural components and their association with other structural components as metadata. In an embodiment of the present invention, the metadata is stored in the form of, but not limited to, one or more master tables, flat files and Extensible Markup Language (XML) files.

In an embodiment of the present invention, the metadata stored in different tables serves different purposes. In an embodiment of the present invention, the metadata stored in the one or more master tables is used for providing source location for capturing additional data. The metadata also comprises unique identifiers for patient parameters. The metadata defines which patient parameter refers to which value. The metadata further provides details of the table from where the referred value is to be obtained and conditions based on which the referred value is to be obtained.

Furthermore, the values of the patient parameters are controlled by flags. The flags associated with a specific patient parameter are used to control updating and purging intervals of the values associated with the patient parameter. In addition, flags are also used to handle movement to next conditions, jump to specific condition and exit points when a workflow is active. The metadata also comprises one or more pre-stored rules, software logic and codes that facilitate storing the metadata for further use and dynamically generating steps of the one or more workflows on one or more client devices. In an embodiment of the present invention, the one or more pre-stored rules define relationships between various data sets, data values and data sources.

At step 408, the stored metadata is synchronized with the one or more client devices to define the one or more workflows in the one or more client devices. In an embodiment of the present invention, the one or more client devices include, but not limited to, smartphones, tablets, smart watches, wearable computing devices, laptops, desktops and personal digital assistants (PDAs). In another embodiment of the present invention, the one or more client devices are specially manufactured to facilitate the one or more healthcare providers to implement clinical workflows while attending to the one or more patients. In various embodiments of the present invention, the one or more client devices may have any operating system including, but not limited to, iOS, android, Windows, Ubuntu and Firefox.

In an embodiment of the present invention, the one or more client devices comprise a workflow application. Further, the workflow application comprises a customized Software Development Kit (SDK). The SDK synchronizes the metadata in the server with the one or more client devices during workflow application set-up phase. In an embodiment of the present invention, the SDK facilitates in designing a repository which is similar to the server repository containing the metadata. During synchronization, the repository at the server is replicated at the one or more client devices thereby replicating the metadata along with the one or more pre-stored rules, software logic and codes. Further, synchronizing the metadata in the server with the one or more client devices ensures that the workflow application is available even if the one or more client devices are offline and not connected with the server. Furthermore, the metadata stored in the one or more client devices is compact and therefore consumes minimal system resources.

The SDK also establishes relationships between various tables and facilitates designing and creating one or more transactional tables. In an embodiment of the present invention, the one or more transactional tables store intermediate information associated with the one or more clinical workflows. The intermediate information associated with the one or more workflows includes, but not limited to, additional information provided by the one or more healthcare providers when the one or more clinical workflows are initiated, measurements and patient parameters from one or more medical devices and other healthcare enterprise systems such as, but not limited to, laboratory information system and imaging systems. In an embodiment of the present invention, the one or more medical devices include, but are not limited to, thermometer, blood pressure measuring device, electrocardiography device, pulse oximeter and arterial blood gas measurement device. The one or more transactional tables also store information related to functioning of a specific clinical workflow. In an embodiment of the present invention, the one or more transactional tables are periodically synchronized with the server for storage and retrieval of the information via a push mechanism.

Once the one or more workflows are defined on the one or more client devices, the workflow application set-up is complete and the one or more defined workflows can be customized based on one or more patient parameters.

At step 410, values of the one or more patient parameters are received. In an embodiment of the present invention, the one or more patient parameters include, but not limited to, body temperature, blood pressure, heart rate, blood glucose level, and blood oxygen level. In an embodiment of the present invention, the values of the patient parameters are received from the one or more healthcare providers. In another embodiment of the present invention, the values of the one or more patient parameters are received from the one or more medical devices.

At step 412, each of the received values of the one or more patient parameters are matched with pre-stored reference values for triggering the one or more defined workflows. In an embodiment of the present invention, the pre-stored reference values for triggering the one or more workflows are stored as metadata in the one or more client devices during synchronization. In an embodiment of the present invention, the SDK facilitates in fetching the pre-stored reference values from the repository and matching the fetched pre-stored reference values with the received values of the one or more patient parameters. In an embodiment of the present invention, the SDK compares the pre-stored reference values with the received values at pre-determined intervals. In another embodiment of the present invention, the matching is performed by the SDK whenever a new value of the patient parameter is received. In an embodiment of the present invention, the pre-stored reference value for triggering a defined workflow is a single value. In another embodiment of the present invention, the pre-stored reference value for triggering a defined workflow is a range of values.

At step 414, a check is performed to ascertain if the received values of the one or more patient parameters match with a pre-stored reference value for triggering a defined workflow. If any of the received value of a patient parameter matches a pre-stored reference value, then at step 416 the defined workflow associated with the matched pre-stored reference value is triggered. In an embodiment of the present invention, the SDK provides an indication to the one or more healthcare providers attending to the one or more patients that the particular clinical workflow has been triggered by rendering an appropriate user interface screen on display of the one or more client devices.

In an embodiment of the present invention, if the received values of the one or more patient parameters do not match any of the pre-stored reference value for triggering the one or more workflows, then the control returns to step 410.

At step 418, one or more steps of the triggered workflow are rendered on the one or more client devices. The one or more steps of the workflow are determined using at least one of: the synchronized metadata corresponding to the triggered workflow and additional information received from at least one of: the one or more healthcare providers and the one or more medical devices. In an embodiment of the present invention, the SDK processes the additional information using the synchronized metadata associated with the triggered workflow for dynamically generating and rendering steps of the triggered clinical workflow on the one or more client devices until an exit condition for the triggered workflow is reached. The SDK also stores the steps of the triggered workflow along with the outcome for future use and records time stamp of each step of the triggered workflow.

In an embodiment of the present invention, the SDK is configured to generate the one or more user interface screens associated with various steps of the triggered workflow using the synchronized metadata related to the one or more user interface screens. The SDK modifies a standard User Interface (UI) template dynamically based on the synchronized metadata to generate one or more UI screens of the triggered workflow, wherein the standard UI template is modified by applying one or more pre-stored UI generation rules and one or more pre-stored rules related to user interaction elements. The SDK then renders the generated one or more UI screens on the one or more client devices.

In an exemplary embodiment of the present invention, clinical workflow for diagnosis of medical conditions such as arrhythmia, hemorrhage, pneumothorax, sepsis, hypervolemia and anxiety is triggered when heart rate value of the patient exceeds the pre-stored trigger value of 110. The healthcare provider attending to the patient is then prompted to provide additional information about the patient such as mental status and systolic blood pressure via the user interface screen rendered on the client device. In an embodiment of the present invention, the healthcare provider clicks the altered mental status tab or radio button on the user interface screen if the mental status of the patient is not normal. In an embodiment of the present invention, the healthcare provider clicks the normal mental status tab or radio button on the user interface screen if the patient's mental status is assessed to be normal by the healthcare provider. In an embodiment of the present invention, the healthcare provider also provides systolic blood pressure value. In another embodiment of the present invention, the systolic blood pressure value is received directly from a blood pressure measuring device. If the mental status of the patient is altered and the systolic blood pressure is less than 90 then the healthcare provider will be advised to call for urgent back-up and assistance and the workflow will end. If the mental status of the patient is normal and the systolic blood pressure is greater than or equal to the reference value of 90 mmHg then the clinical workflow suggests alternate pathway which involves further actions such as performing ECG, performing Arterial Blood Gas (ABG) test and assessing heart rhythm. The clinical workflow then continues based on outcomes of previous steps. The values entered by the healthcare provider are analyzed using the stored metadata. One or more steps and actions that the healthcare provider should initiate such as, but not limited to, perform ECG, measure calf pressure and perform an arterial blood gas test are then rendered on the client device. Eventually, the clinical workflow reaches an exit condition and is recorded. The exit condition indicates the end of the clinical workflow. In an embodiment of the present invention, the exit condition include, but is not limited to, diagnosis of a disorder, administering medicine, referring the patient to a specialist and seeking further instructions and opinions from other healthcare providers.

In an exemplary embodiment of the present invention, clinical workflow for diagnosis of medical conditions such as pneumothorax, flash pulmonary edema, myocardial infarction, aspiration pneumonia, pulmonary embolism, bronchospasm and atelectasis is triggered when oxygen saturation value is less than 90 and plasma saturation value is less than 60. The one or more healthcare providers are then prompted to provide additional information about the patient such as mental status and systolic blood pressure via the user interface screen rendered on the client device. The clinical workflow continues based on outcomes of previous steps. The healthcare provider may be prompted to provide additional information. The clinical workflow may involve additional checks and alternate pathways. Eventually, the medical condition of the patient is diagnosed and the workflow is completed and recorded.

Figure 5:
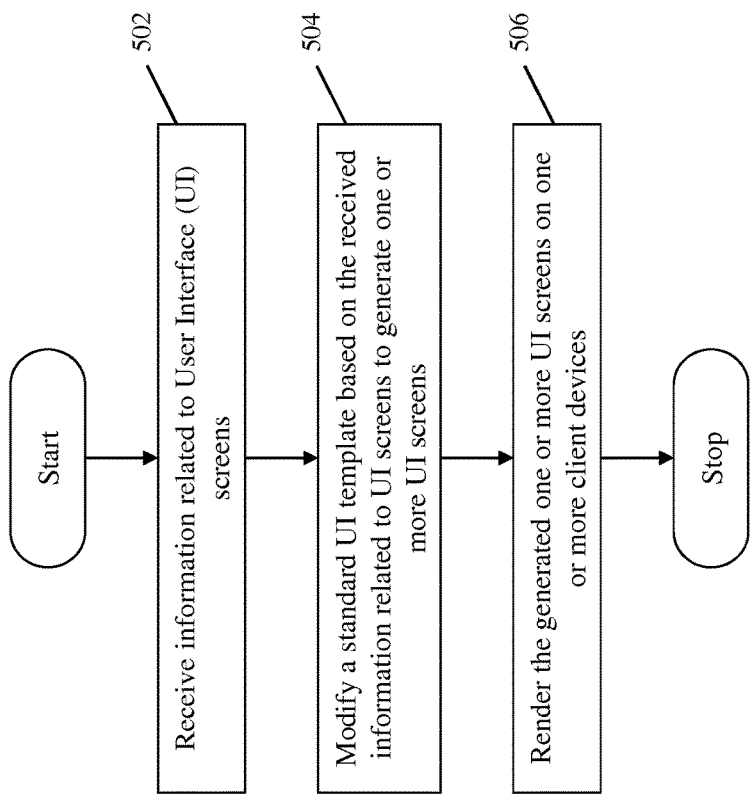
FIG. 5 represents a flowchart of a method for generating user interface screens, in accordance with an embodiment of the present invention.

FIG. 5 represents a flowchart of a method for generating user interface screens, in accordance with an embodiment of the present invention.

At step 502, information related to User Interface (UI) screens of one or more applications is received. In an embodiment of the present invention, one or more users provide information related to UI screens via a user interface at a server-end. In an embodiment of the present invention, the received information related to UI screens include, but is not limited to, number of user interaction elements, type of user interaction elements, placement of user interaction elements, configuration information for the user interaction elements, order in which the user interaction elements need to be generated and a unique identifier for storing and retrieving the received data related to the UI screens. In an embodiment of the present invention, one or more user interaction elements include, but are not limited to, radio buttons, banners, text box, list boxes, check boxes, drop-down list, window, datagrid, slider, icons and menu bar. The received information is stored in a repository at the server-end.

In an embodiment of the present invention, the one or more users fill one or more standard UI templates. The one or more users then save the filled template with a unique identification name and description of UI screen in the repository. In an embodiment of the present invention, the one or more standard UI templates are blank UI screens on which one or more user interaction elements are placed. Further, each of the one or more standard UI templates have its configuration and attribute details pre-stored in the repository as metadata. The repository also comprises metadata for generating the one or more UI screens. Further, the metadata and the received information in the repository at the server-end is synchronized with one or more client devices for dynamically generating the one or more UI screens. In an embodiment of the present invention, a UI Software Development Kit (SDK), at the one or more client devices, facilitates in designing a repository at client-end for synchronizing the metadata and the received information.

At step 504, a standard UI template is modified dynamically based on the received information to generate one or more UI screens. The standard UI template is modified by applying one or more UI generation rules and one or more rules related to user interaction elements based on the received information. The synchronized metadata is used for modifying the UI template. The synchronized metadata for generating the one or more UI screens comprise, but not limited to, one or more standard UI templates, identification name and configuration details of various user interaction elements, one or more UI generation rules and one or more rules related to user interaction elements. In an embodiment of the present invention, the one or more UI generation rules comprise, but not limited to, rules for suitably structuring and placing user interaction elements on the UI screens. In an embodiment of the present invention, the one or more rules related to user interaction elements comprise, but not limited to, rules related to placement and configurations of each user interaction element. The one or more UI generation rules and the one or more rules related to user interaction elements are configurable.

The UI SDK also facilitates creating one or more transactional tables at the one or more client devices. The one or more transactional tables are configured to store information related to user interaction. In an embodiment of the present invention, the one or more transactional tables store the unique identification name and description of the UI screens.

When a user accesses an application on the one or more client devices, the received information and the synchronized metadata associated with the UI screens of the application being accessed are retrieved from the repository at the client end. Further, a standard UI template and its corresponding configuration and attribute details are retrieved from the repository at the client-end. Furthermore, the configuration details related to the type of the user interaction elements to be placed on the UI screen being generated are retrieved. Also, the one or more UI generation rules and the one or more rules related to the user interaction elements to be placed on the UI screen are retrieved. The retrieved standard UI template is then modified by placing the user interaction elements suitably based on the received placement information of the user interaction elements. Also, the retrieved one or more UI generation rules and the one or more rules related to the user interaction elements are applied on the modified UI template. The retrieved configuration and attribute details of the standard UI template are also modified by adding the retrieved configuration details of the user interaction elements being placed on the standard UI template. The UI screen is thereby dynamically generated along with its configuration and attribute details for the one or more applications.

At step 506, the generated one or more UI screens are rendered on one or more client devices when the one or more users access the one or more applications. In an embodiment of the present invention, the UI screens are dynamically generated for the one or more healthcare applications. In an embodiment of the present invention, UI screens for providing the steps of the one or more clinical workflows are generated in real-time while a triggered workflow is in progress.

Figure 6:
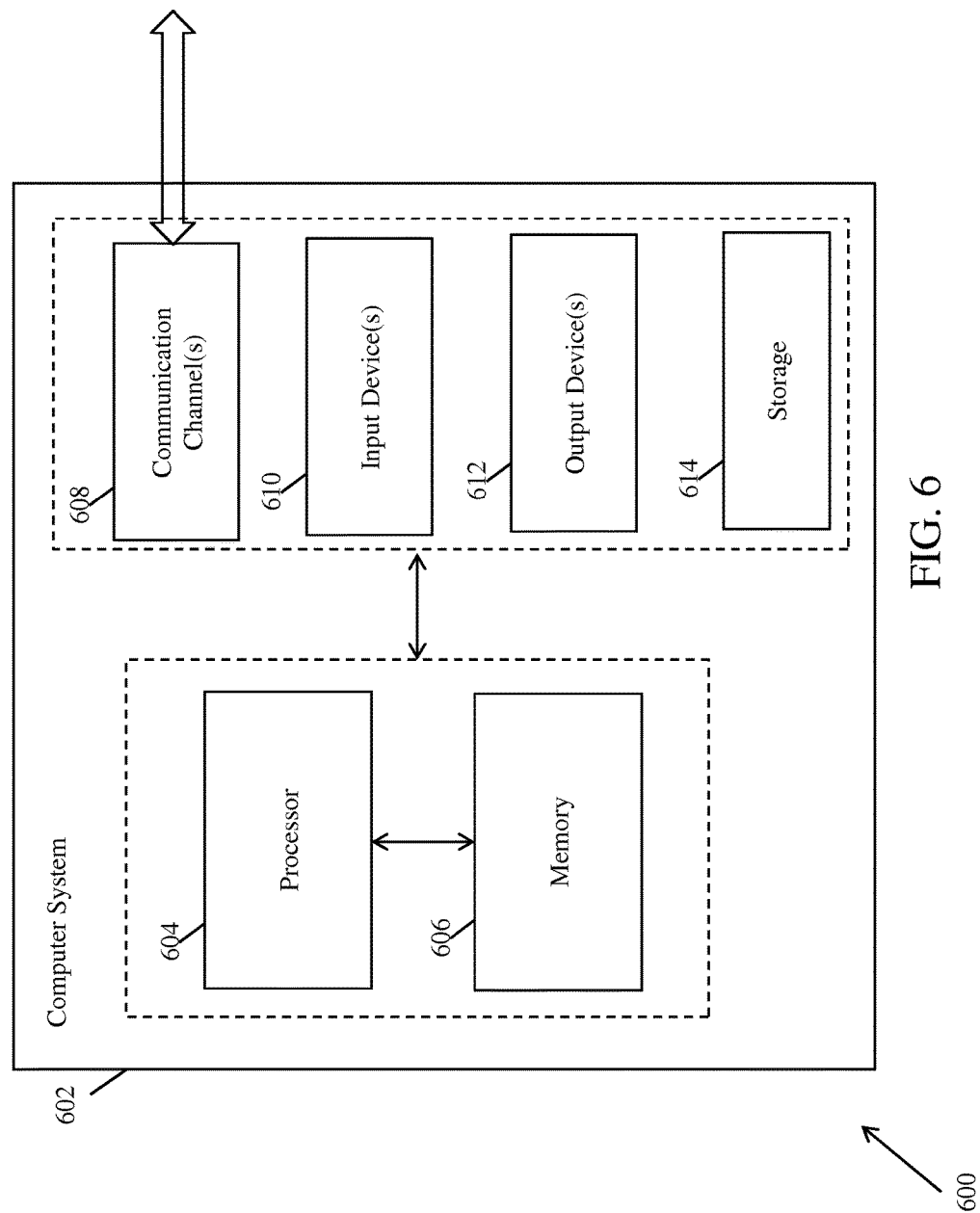
FIG. 6 illustrates an exemplary computer system for defining clinical workflows and generating user interface screens, in accordance with an embodiment of the present invention.

FIG. 6 illustrates an exemplary computer system for defining clinical workflows and generating user interface screens, in accordance with an embodiment of the present invention.

The computer system 602 comprises a processor 604 and a memory 606. The processor 604 executes program instructions and may be a real processor. The processor 604 may also be a virtual processor. The computer system 602 is not intended to suggest any limitation as to scope of use or functionality of described embodiments. For example, the computer system 602 may include, but not limited to, a general-purpose computer, a programmed microprocessor, a micro-controller, a peripheral integrated circuit element, and other devices or arrangements of devices that are capable of implementing the steps that constitute the method of the present invention. In an embodiment of the present invention, the memory 606 may store software for implementing various embodiments of the present invention. The computer system 602 may have additional components. For example, the computer system 602 includes one or more communication channels 608, one or more input devices 610, one or more output devices 612, and storage 614. An interconnection mechanism (not shown) such as a bus, controller, or network, interconnects the components of the computer system 602. In various embodiments of the present invention, operating system software (not shown) provides an operating environment for various softwares executing in the computer system 602, and manages different functionalities of the components of the computer system 602.

The communication channel(s) 608 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, Bluetooth or other transmission media.

The input device(s) 610 may include, but not limited to, a keyboard, mouse, pen, joystick, trackball, a voice device, a scanning device, or any another device that is capable of providing input to the computer system 602. In an embodiment of the present invention, the input device(s) 610 may be a sound card or similar device that accepts audio input in analog or digital form. The output device(s) 612 may include, but not limited to, a user interface on CRT or LCD, printer, speaker, CD/DVD writer, or any other device that provides output from the computer system 602.

The storage 614 may include, but not limited to, magnetic disks, magnetic tapes, CD-ROMs, CD-RWs, DVDs, flash drives or any other medium which can be used to store information and can be accessed by the computer system 602. In various embodiments of the present invention, the storage 614 contains program instructions for implementing the described embodiments.

The present invention may suitably be embodied as a computer program product for use with the computer system 602. The method described herein is typically implemented as a computer program product, comprising a set of program instructions which is executed by the computer system 602 or any other similar device. The set of program instructions may be a series of computer readable codes stored on a tangible medium, such as a computer readable storage medium (storage 614), for example, diskette, CD-ROM, ROM, flash drives or hard disk, or transmittable to the computer system 602, via a modem or other interface device, over either a tangible medium, including but not limited to optical or analogue communications channel(s) 608. The implementation of the invention as a computer program product may be in an intangible form using wireless techniques, including but not limited to microwave, infrared, bluetooth or other transmission techniques. These instructions can be preloaded into a system or recorded on a storage medium such as a CD-ROM, or made available for downloading over a network such as the internet or a mobile telephone network. The series of computer readable instructions may embody all or part of the functionality previously described herein.

The present invention may be implemented in numerous ways including as an apparatus, method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

We claim:

1. A computer-implemented method for defining clinical workflows, via program instructions stored in a memory and executed by a processor, the computer-implemented method comprising:
receiving, at a server-end, information related to one or more clinical workflows;
translating the received information into a machine readable language, wherein the received information is translated by splitting the received information into one or more structural components and translating each of the one or more structural components;
storing the translated information as metadata, wherein the step of storing the translated information as the metadata comprises storing the translated information for each of the one or more structural components and their association with other structural components as the metadata, wherein the metadata comprises one or more flags to control one or more predefined values corresponding to one or more patient parameters such that flags facilitate triggering of one or more clinical workflows, on one or more client devices, when the one or more predefined values match with values of the one or more patient parameters received at the one or more client devices; and
synchronizing the stored metadata with one or more client devices, communicatively coupled to the server-end, to define the one or more clinical workflows in the one or more client devices, wherein the one or more defined clinical workflows are dynamically customized based on one or more patient parameters, further wherein synchronization facilitates defining and customization of the one or more clinical workflows on the one or more client devices when the one or more client devices are not connected with the server-end.

2. The computer-implemented method of claim 1 further comprising:
receiving, at the one or more client devices, values of the one or more patient parameters from at least one of: one or more healthcare providers and one or more medical devices;
matching each of the received values of the one or more patient parameters with pre-stored reference values for triggering the one or more defined workflows, wherein the synchronized metadata comprises the pre-stored reference values for triggering;
triggering a defined workflow associated with the pre-stored reference value that matches at least one of the received value of the at least one parameter; and
rendering one or more steps of the triggered workflow using at least one of: the synchronized metadata corresponding to the triggered workflow and additional information received from at least one of: the one or more healthcare providers and the one or more medical devices.

3. The computer-implemented method of claim 2, wherein the step of rendering the one or more steps of the triggered workflow comprises:
modifying a standard User Interface (UI) template dynamically based on the synchronized metadata to generate one or more UI screens of the triggered workflow, wherein the standard UI template is modified by applying one or more pre-stored UI generation rules and one or more pre-stored rules related to user interaction elements; and
rendering the generated one or more UI screens on the one or more client devices.

4. The computer-implemented method of claim 1, wherein the received information related to the one or more clinical workflows comprise at least one of: one or more trigger conditions, one or more reference values for triggering, one or more pathways, one or more clinical rules, one or more business rules, one or more exit conditions and information related to one or more User Interface (UI) screens associated with each of the one or more clinical workflows.

5. The computer-implemented method of claim 1, wherein the one or more patient parameters comprise: body temperature, blood pressure, heart rate, blood glucose level, and blood oxygen level.

6. The computer-implemented method of claim 2, wherein the one or more healthcare providers comprise doctors, specialists, nurses and clinicians.

7. The computer-implemented method of claim 2, wherein the one or more medical devices comprise thermometer, blood pressure measuring device, electrocardiography device, glucometer, pulse oximeter and arterial blood gas measurement device.

8. A system for defining clinical workflows, the system comprising:
a user interface, at a server-end, configured to receive information related to one or more clinical workflows;
an interpreter configured to translate the received information into a machine readable language, wherein the received information is translated by splitting the received information into one or more structural components and translating each of the one or more structural components;
a metadata convertor configured to store the translated information as metadata in a server metadata repository, wherein storing the translated information as the metadata comprises storing the translated information for each of the one or more structural components and their association with other structural components as the metadata, wherein the metadata comprises one or more flags to control one or more predefined values corresponding to one or more patient parameters such that flags facilitate triggering of one or more clinical workflows, on one or more client devices, when the one or more predefined values match with values of the one or more patient parameters received at the one or more client devices; and
a workflow configuration engine configured to synchronize the stored metadata with one or more client devices, communicatively coupled to the server-end, to define one or more clinical workflows in the one or more client devices, wherein the one or more defined workflows are dynamically customized based on one or more patient parameters, further wherein the synchronization facilitates defining and customization of the one or more clinical workflows on the one or more client devices when the one or more client devices are not connected with the server-end.

9. The system of claim 8, wherein the synchronization at the one or more client devices is facilitated by a Software Development Kit (SDK), the SDK comprises:
a client user interface configured to receive values of the one or more patient parameters from at least one of: one or more healthcare providers and one or more medical devices; and
a workflow processing engine configured to:
match each of the received values of the one or more patient parameters with pre-stored reference values for triggering the one or more defined workflows, wherein the synchronized metadata comprises the pre-stored reference values for triggering;

trigger a defined workflow associated with the pre-stored reference value that matches at least one of the received value of the at least one parameter; and render one or more steps of the triggered workflow using at least one of:

the synchronized metadata associated with the triggered workflow and additional information received from at least one of: the one or more healthcare providers and the one or more medical devices.

10. The system of claim 9, wherein rendering the one or more steps of the triggered workflow comprises:

modifying a standard User Interface (UI) template dynamically based on the synchronized metadata to generate one or more UI screens of the triggered workflow, wherein the standard UI template is modified by applying one or more pre-stored UI generation rules and one or more pre-stored rules related to user interaction elements; and rendering the generated one or more UI screens on the one or more client devices.

11. The system of claim 8, wherein the received information related to the one or more clinical workflows comprise at least one of: one or more trigger conditions, one or more reference values for triggering, one or more pathways, one or more clinical rules, one or more business rules, one or more exit conditions, and information related to one or more User Interface (UI) screens associated with each of the one or more clinical workflows.

12. The system of claim 8, wherein the one or more patient parameters comprise: body temperature, blood pressure, heart rate, blood glucose level, and blood oxygen level.

13. The system of claim 9, wherein the one or more healthcare providers comprise doctors, specialists, nurses and clinicians.

14. The system of claim 9, wherein the one or more medical devices comprise thermometer, blood pressure measuring device, electrocardiography device, glucometer, pulse oximeter and arterial blood gas measurement device.

15. A computer program product for defining clinical workflows, the computer program product comprising:

a non-transitory computer-readable medium having computer-readable program code stored thereon, the computer-readable program code comprising instructions that when executed by a processor, cause the processor to:

receive, at a server-end, information related to one or more clinical workflows;

translate the received information into a machine readable language, wherein the received information is translated by splitting the received information into one or more structural components and translating each of the one or more structural components;

store the translated information as metadata, wherein the step of storing the translated information as the metadata comprises storing the translated information for each of the one or more structural components and their association with other structural components as the metadata, wherein the metadata comprises one or more flags to control one or more predefined values corresponding to one or more patient parameters such that flags facilitate triggering of one or more clinical workflows, on one or more client devices, when the one or more predefined values match with values of the one or more patient parameters received at the one or more client devices; and synchronize the stored metadata with one or more client devices, communicatively coupled to the server-end, to define the one or more clinical workflows in the one or more client devices, wherein the one or more defined clinical workflows are dynamically customized based on one or more patient parameters, further wherein synchronizing facilitates defining and customization of the one or more clinical workflows, at the one or more client devices, when the one or more client devices are not connected with the server-end.

16. The computer program product of claim 15 further comprising:

receiving, at the one or more client devices, values of the one or more patient parameters from at least one of: one or more healthcare providers and one or more medical devices;

matching each of the received values of the one or more patient parameters with pre-stored reference values for triggering the one or more defined workflows, wherein the synchronized metadata comprises the pre-stored reference values for triggering;

triggering a defined workflow associated with the pre-stored reference value that matches at least one of the received value of the at least one parameter; and rendering one or more steps of the triggered workflow using at least one of: the synchronized metadata corresponding to the triggered workflow and additional information received from at least one of: the one or more healthcare providers and the one or more medical devices.

* * * * *